(12) United States Patent
Caponigro et al.

(10) Patent No.: US 9,867,825 B2
(45) Date of Patent: *Jan. 16, 2018

(54) PHARMACEUTICAL COMBINATION COMPRISING BINIMETINIB

(71) Applicant: Novartis AG, Basel (CH)

(72) Inventors: Giordano Caponigro, Cambridge, MA (US); Scott Delach, Cambridge, MA (US); Shivang Doshi, Cambridge, MA (US); Thomas Horn-Spirohn, Cambridge, MA (US); Sunkyu Kim, Cambridge, MA (US)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/651,297

(22) PCT Filed: Dec. 16, 2013

(86) PCT No.: PCT/IB2013/060999
§ 371 (c)(1),
(2) Date: Jun. 11, 2015

(87) PCT Pub. No.: WO2014/097125
PCT Pub. Date: Jun. 26, 2014

(65) Prior Publication Data
US 2015/0313902 A1    Nov. 5, 2015

Related U.S. Application Data

(60) Provisional application No. 61/740,225, filed on Dec. 20, 2012.

(51) Int. Cl.
A61K 31/519 (2006.01)
A61K 31/4184 (2006.01)

(52) U.S. Cl.
CPC ........ *A61K 31/519* (2013.01); *A61K 31/4184* (2013.01)

(58) Field of Classification Search
CPC .................................................... A61K 31/519
See application file for complete search history.

(56) References Cited

U.S. PATENT DOCUMENTS

| 7,235,537 B2 * | 6/2007 | Wallace ................. C04B 35/632 514/80 |
| 2012/0115878 A1 | 5/2012 | Calienni et al. |
| 2015/0164897 A1 * | 6/2015 | Caponigro ........... A61K 31/519 514/252.16 |

FOREIGN PATENT DOCUMENTS

| WO | 03077914 | 9/2003 |
| WO | 2005058341 | * 6/2005 |
| WO | 2007140222 | * 12/2007 |
| WO | 2010020675 | * 2/2010 |

OTHER PUBLICATIONS

Li Jing et al., Cancer Investigation, vol. 28, No. 4, pp. 350-356, 2010.*

* cited by examiner

*Primary Examiner* — Karl J Puttlitz
(74) *Attorney, Agent, or Firm* — Jennifer Chapman (57) ABSTRACT

A combination of a CDK4/6 inhibitor and a MEK inhibitor for the treatment of diseases such as cancer.

12 Claims, 9 Drawing Sheets

Compound A + Compound B combination in MEL-JUSO

Figure 1A. Compound A + Compound B combination in MEL-JUSO

Figure 1B. Compound A + Compound B combination in Hs 944.T

Figure 1C. Compound A + Compound B combination in SK-MEL-2

Figure 1D. Compound A + Compound B combination in SK-MEL-30

Figure 1E. Compound A + Compound B combination in IPC-298

Figure 2. Tumor growth of Hs 944.T xenograft treated with Compound A

Figure 3. Tumor growth of MEL-JUSO xenografts treated with Compound A

Figure 4. Tumor growth of MEL-JUSO xenografts treated with Compound A

Figure 5 Tumor growth of MEL-JUSO xenografts treated with Compound A and Compound B combination

PHARMACEUTICAL COMBINATION COMPRISING BINIMETINIB

FIELD OF THE INVENTION

A combination of (a) a cyclin dependent kinase 4/6 (CDK4/6) inhibitor compound, or a pharmaceutically acceptable salt thereof, and (b) a mitogen activated protein kinase (MEK) inhibitor compound, or a pharmaceutically acceptable salt thereof, for the treatment of solid tumors and hematological malignancies. This invention also relates to the use of the combination thereof, in the management of hyperproliferative diseases such as cancer.

BACKGROUND OF THE INVENTION

Tumor development is closely associated with genetic alteration and deregulation of CDKs and their regulators, suggesting that inhibitors of CDKs may be useful anticancer therapeutics. Indeed, early results suggest that transformed and normal cells differ in their requirement for, e.g., cyclin D/CDK4/6 and that it may be possible to develop novel antineoplastic agents devoid of the general host toxicity observed with conventional cytotoxic and cytostatic drugs.

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

At a molecular level mediation of CDK/cyclin complex activity requires a series of stimulatory and inhibitory phosphorylation, or dephosphorylation, events. CDK phosphorylation is performed by a group of CDK activating kinases (CAKs) and/or kinases such as wee1, Myt1 and Mik1. Dephosphorylation is performed by phosphatases such as cdc25 (a & c), pp2a, or KAP.

CDK/cyclin complex activity may be further regulated by two families of endogenous cellular proteinaceous inhibitors: the Kip/Cip family, or the INK family. The INK proteins specifically bind CDK4 and CDK6. p16$^{ink4}$ (also known as MTS1) is a potential tumour suppressor gene that is mutated, or deleted, in a large number of primary cancers. The Kip/Cip family contains proteins such as p21$^{Cip1,Waf1}$, p27$^{Kip1}$ and p57$^{kip2}$, where p21 is induced by p53 and is able to inactivate the CDK2/cyclin(E/A) complex. A typically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of CDKs, and their associated proteins, in co-ordinating and driving the cell cycle in proliferating cells have been outlined above. Some of the biochemical pathways in which CDKs play a key role have also been described. The development of monotherapies for the treatment of proliferative disorders, such as cancers, using therapeutics targeted generically at CDKs, or at specific CDKs, is therefore potentially highly desirable. Thus, there is a continued need to find new therapeutic agents to treat human diseases.

The CDK inhibitor compound 7-Cyclopentyl-2-(5-piperazin-1-yl-pyridin-2-ylamino)-7H-pyrrolo[2,3-d]pyrimidine-6-carboxylic acid dimethylamide (Compound A) is described in PCT Application No. WO 2010/020675 as Example 74.

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Res results in the activation and indirect phosphorylation of Raf kinase. Raf then phosphorylates MEK1 and 2 on two serine residues (S218 and S222 for MEK1 and S222 and S226 for MEK2) (Ahn et al., Methods in Enzymology 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., Methods in Enzymology 2001, 332, 417-431). Phosphorylated ERK dimerizes and then translocates to the nucleus where it accumulates (Khokhlatchev et al., Cell 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., Molecular Cell 2000, 6, 1343-1354). Overall, treatment of cells with growth factors leads to the activation of ERK1 and 2 which results in proliferation and, in some cases, differentiation (Lewis et al., Adv. Cancer Res. 1998, 74, 49-139).

The MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) is described in PCT Application No. WO 03/077914, and methods for its preparation have been described, for example, in Example 18 therein.

SUMMARY OF THE INVENTION

The invention provides a combination comprising a first agent Compound A or pharmaceutical salt(s) thereof that inhibits the CDK4/6 pathway and a second agent Compound B or pharmaceutical salt(s) thereof that inhibits the MEK pathway. In another aspect, the invention provides combinations including pharmaceutical compositions comprising a therapeutically effective amount of a first agent Compound A or pharmaceutical salt(s) thereof, a second agent Compound B or pharmaceutical salt(s) thereof, and a pharmaceutically acceptable carrier.

Compound A is described by the chemical name: 7-Cyclopentyl-2-(5-piperazin-1-yl-pyridin-2-ylamino)-7H-pyrrolo[2,3-d]pyrimidine-6-carboxylic acid dimethylamide and has the following structure (A):

(A)

Compound B is described by the chemical name: 6-(4-bromo-2-fluorophenylamino)-7-fluoro-3-methyl-3H-benzoimidazole-5-carboxylic acid (2-hydroxyethyoxy)-amide and has the following structure (B):

Furthermore, the present invention provides the use of a combination of a first agent Compound A or pharmaceutical salt(s) thereof, and a second agent Compound B or pharmaceutical salt(s) thereof, in the manufacture of a medicament for treating cancer.

Furthermore, the present invention provides a method of treating cancer using the combination of a first agent Compound A or pharmaceutical salt(s) thereof, and a second agent Compound B or pharmaceutical salt(s) thereof.

The present invention has a therapeutic use in the treatment of cancer. Non-limiting examples of the such cancers include pancreatic cancer, breast cancer, mantle cell lymphoma, non-small cell lung cancer, melanoma, colon cancer, esophageal cancer, liposarcoma, multiple myeloma, T-cell leukemia, renal cell carcinoma, gastric cancer, renal cell carcinoma, glioblastoma, hepatocellular carcinoma, gastric cancer, lung cancer, colon cancer or rhabdoid tumor. In one embodiment, such cancer includesretinoblastoma protein (retinoblastoma tumor suppressor protein or pRb) positive cancers. The above combinations and compositions can be administered to a system comprising cells or tissues, as well as a human patient or and animal subject.

DETAILED DESCRIPTION OF THE INVENTION

The invention provides a combination comprising a first agent Compound A or pharmaceutical salt(s) thereof that inhibits the CDK4/6 pathway and a second agent Compound B or pharmaceutical salt(s) thereof that inhibits MEK pathway. In another aspect, the invention provides combinations including pharmaceutical compositions comprising a therapeutically effective amount of a first agent Compound A or pharmaceutical salt(s) thereof, a second agent Compound B or pharmaceutical salt(s) thereof, and a pharmaceutically acceptable carrier.

Compound A is described by the chemical name: 7-Cyclopentyl-2-(5-piperazin-1-yl-pyridin-2-ylamino)-7H-pyrrolo[2,3-d]pyrimidine-6-carboxylic acid dimethylamide and has the following structure (A):

The preferred salt of the Compound A is the succinate salt.

Compound B is described by the chemical name: 6-(4-bromo-2-fluorophenylamino)-7-fluoro-3-methyl-3H-benzoimidazole-5-carboxylic acid (2-hydroxyethyoxy)-amide and has the following structure (B):

The combination of Compound A and Compound B can be administered simultaneously, separately or sequentially. The combination can be administered in a single dosage form or in separate dosage forms.

The term "a MEK inhibitor" is defined herein to refer to a compound which targets, decreases or inhibits the kinase activity of MAP kinase, MEK. A target of a MEK inhibitor includes, but is not limited to, ERK. An indirect target of a MEK inhibitor includes, but is not limited to, cyclin D1.

The term "pharmaceutical composition" is defined herein to refer to a mixture or solution containing at least one therapeutic agent to be administered to a subject, e.g., a mammal or human, in order to prevent or treat a particular disease or condition affecting the mammal or human.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "co-administration" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease The term "prevent", "preventing" or "prevention" as used herein comprises the prevention of at least one symptom associated with or caused by the state, disease or disorder being prevented.

The term "pharmaceutically effective amount" or "clinically effective amount" of a combination of therapeutic agents is an amount sufficient to provide an observable improvement over the baseline clinically observable signs and symptoms of the disorder treated with the combination.

The term "synergistic effect" as used herein refers to action of two therapeutic agents such as, for example, the CDK inhibitor compound Compound A, and a MEK inhibitor compound of Compound B, producing an effect, for example, slowing the symptomatic progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from cancers.

The term about" or "approximately" shall have the meaning of within 10%, more preferably within 5%, of a given value or range.

The diseases or condition treated by the present invention include but are not limited to breast cancer (ER+, ER−), genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; leukemias, hyperplasias, stomach cancer, colon cancer, larynx cancer, lymphatic system, genitourinary tract, bone, prostate, non-small-cell lung, glioma, colorectal; kidney, epidermas, liver, esophagus, hematopoietic, lymphoma, myeloma, thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma; chronic lymphocytic leukaemia, mantle cell lymphoma, large B cell lymphoma; and rhabdoid tumor.

The combinations and compositions can be administered to a system comprising cells or tissues, as well as a human patient or and animal subject.

The combination and composition of the present invention can be administered in various dosage forms and strength, in pharmaceutically effective amount or clinically effective amount. For example, for human subjects, the combination can be administered 45 mg BID for Compound B and 200 mg QD for Compound A.

The pharmaceutical compositions for separate administration of both combination partners, or for the administration in a fixed combination, i.e. a single galenical composition comprising the combination, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers, especially suitable for enteral or parenteral application.

The novel pharmaceutical composition contains may contain, from about 0.1% to about 99.9%, preferably from about 1% to about 60%, of the therapeutic agent(s). Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients, 4$^{th}$ edition*, Rowe et al., Eds., American Pharmaceuticals Association (2003); and *Remington: the Science and Practice of Pharmacy*, 20th edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The invention is illustrated by the following non-limiting examples.

EXAMPLES

Example 1

The oncogenic drivers in a sizable fraction of melanomas are mutant alleles of NRAS that encode one of several variants at position Q61 in the protein. Similar to activated alleles of BRAF, these alleles encode constitutively activated forms of the protein that drive signaling through the MAPK pathway. One consequence of the activation of MAPK signaling is the elevation of cyclin D1 levels that help drive cell cycle progression. Accordingly, inhibitors of the MEK1/2 proteins which occupy a central position in the MAPK pathway have been shown to inhibit the growth of NRAS-mutant cell lines and xenograft models of melanoma. Based on these observations, the single agent and combination effects of Compound A, and the MEK1/2 inhibitor Compound B, on the in vivo proliferation of MEL-JUSO melanoma model, harboring mutant alleles of NRAS was studied. As shown in Table 1, Compound A and Compound B inhibited the tumor growth as single agents in NRAS mutant melanomas. Moreover, combining Compound A with Compound B led to enhanced tumor growth inhibition, when compared to their single agent activities, suggesting that the combination may produce higher anti-tumor activities (Table 1). T/C % is defined as the mean change in tumor volume from the time of treatment initiation to the end of study. The % regression is calculated as $100 \times \Delta T/Tinitial$ if $\Delta T < 0$. Complete regression is defined as non-palpable tumor.

TABLE 1

Summary results of Compound A and Compound B efficacy in MEL-JUSO xenografts

| Treatment | T/C (%) | Regression (%) | Change in tumor volume (mm$^3$, mean ± SEM) | Change in body weight (%, mean ± SEM) | Survival |
|---|---|---|---|---|---|
| Vehicle | 100 | | 497 ± 67 | −4.4 ± 2.1 | 6/6 |
| Compound A [150 mg/kg qd] | 32 | | 157 ± 33 | −3.9 ± 2.1 | 6/6 |
| Compound A [250 mg/kg qd] | 2 | | 9 ± 11 | −2.7 ± 1.6 | 6/6 |
| Compound B [3.5 mg/kg bid] | 12 | | 59 ± 24 | −0.3 ± 2.1 | 6/6 |

TABLE 1-continued

Summary results of Compound A and Compound B efficacy in MEL-JUSO xenografts

| Treatment | T/C (%) | Regression (%) | Change in tumor volume (mm$^3$, mean ± SEM) | Change in body weight (%, mean ± SEM) | Survival |
|---|---|---|---|---|---|
| Compound A [150 mg/kg qd] + Compound B [3.5 mg/kg bid] | | 34 | −42 ± 8 | 6.2 ± 2.0 | 6/6 |

Tumor growth inhibition is indicated by either % T/C or % regression. Compound A, as a single agent given at 150 mg/kg, qd, and 250 mg/kg, qd, doses, inhibited tumor growth of the MEL-JUSO NRAS mutant model. Compound B, as a single agent given at 3.5 mg/kg, bid, dose, inhibited the tumor growth.
The combination of Compound A and Compound B, at 150 mg/kg, qd, and 3.5 mg/kg, bid, doses respectively, produced 34% regression.

Example 2

Three melanoma cell lines, MEL-JUSO, SK-MEL2 and Hs 944.T, which harbor the Q61X activating mutation of NRAS, were tested with Compound A and Compound B to measure their sensitivity to the inhibitors. As Table 2 shows, when measured via BrdU uptake assay, both Compound A and Compound B inhibited the growth of all three cell lines, demonstrating that the two compounds have single agent activities in the cells.

TABLE 2

BrdU IC50 (µM) of Compound A and Compound B in melanoma cells with activated NRAS

| | BrdU IC50 (uM) | |
|---|---|---|
| | Compound A | Compound B |
| MEL-JUSO | 0.36 | 0.024 |
| SK-MEL2 | 0.75 | 0.99 |
| Hs 944.T | 3.83 | 0.554 |

To determine if combining Compound A and Compound B would lead to enhanced growth inhibition, MEL-JUSO, Hs 944.T, SK-MEL-2, SK-MEL-30, and IPC-298 cells were treated with combinations of Compound A and Compound B, and evaluated for inhibitions observed for single agents vs. combinations. The MEL-JUSO and the Hs 944.T cells are evaluated with CTG assays. The SK-MEL-2, SK-MEL-30, and IPC-298 cells are evaluated with microscopy based assays. As shown in FIGS. 1A-1E, all 5 cell lines showed inhibitions above simple additivity via both ADD excess inhibition calculations and isobologram visualizations. The synergy score of >2 indicates growth inhibitions beyond the sum of single agent activities. The synergy scores suggest that the two agents, when combined, can produce growth inhibitions greater than the sum of the individual activities of Compound A and Compound B, and support further exploration of the combination in in-vivo studies.

The Synergy scores for the combinations:

| Cell Line | Synergy Score |
|---|---|
| MEL-JUSO | 7.63 |
| Hs 944.T | 2.12 |
| SK-MEL-2 | 3.52 |
| SK-MEL-30 | 2.39 |
| IPC-298 | 3.12 |

Example 3

Anti-Tumor Efficacy of Compound A in Hs 944.T and MEL-JUSO Melanoma Xenografts

Figure 1A:
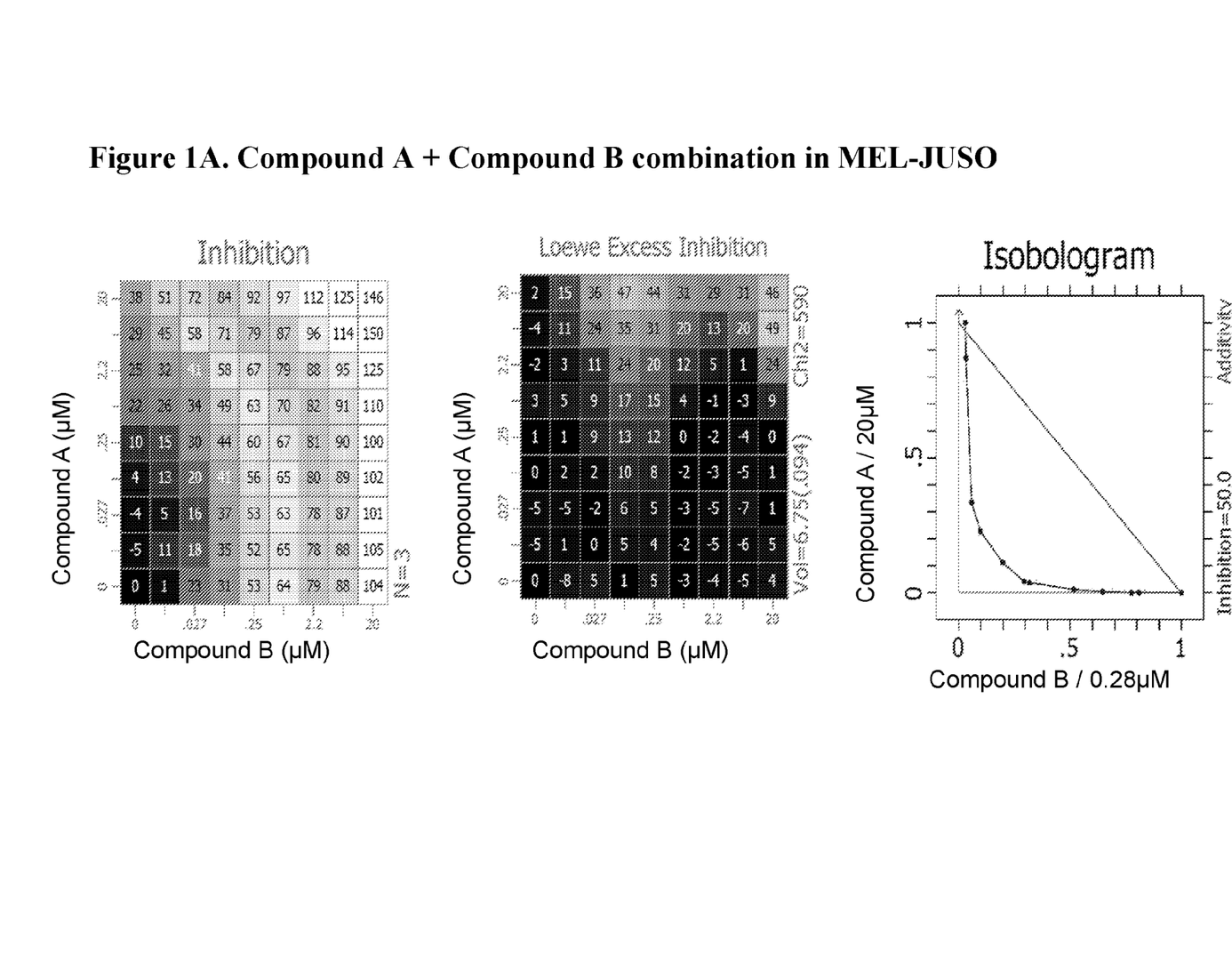
FIGS. 1A-1E show Compound A and Compound B combination produces a synergistic effect in inhibiting in various mutant melanomas.
Figure 1B:
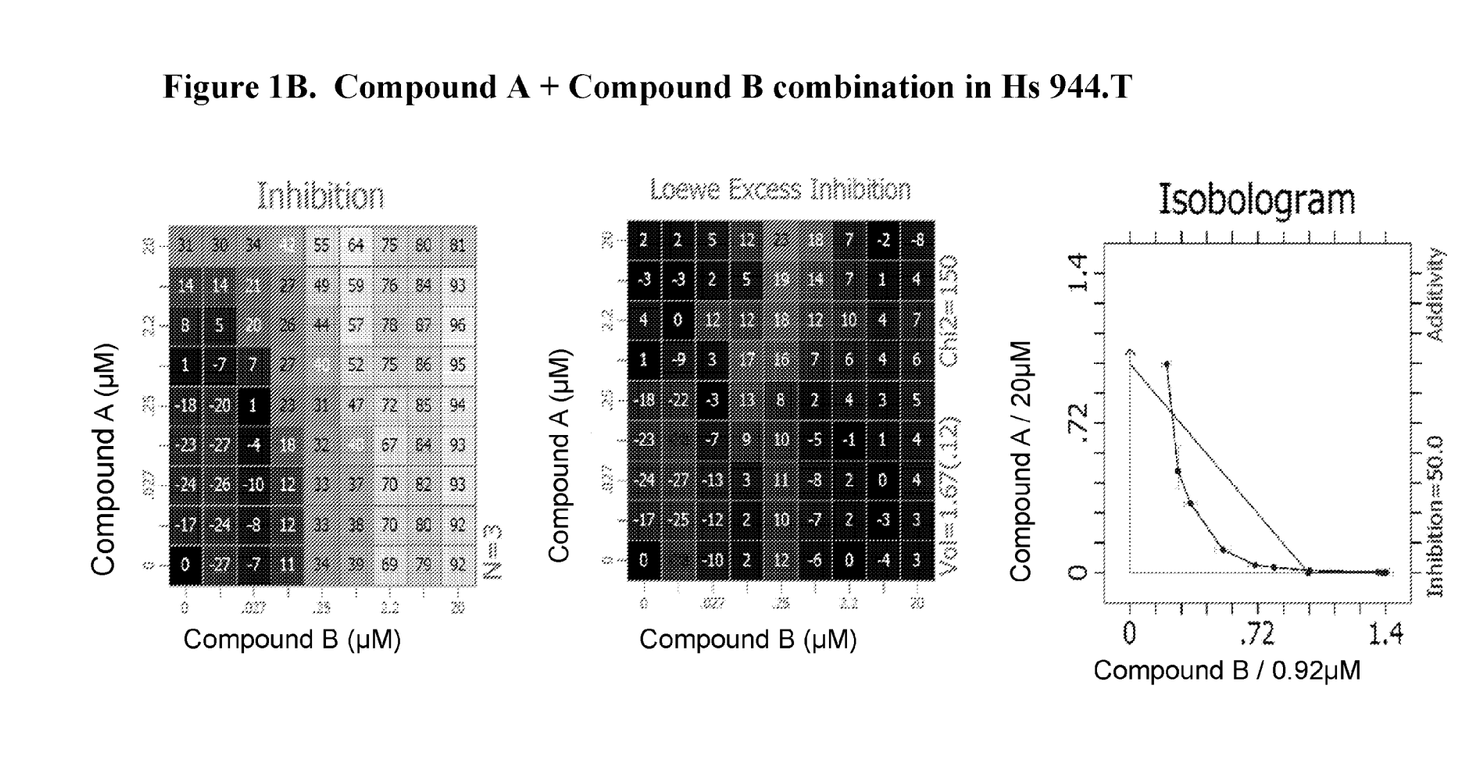
Figure 1C:
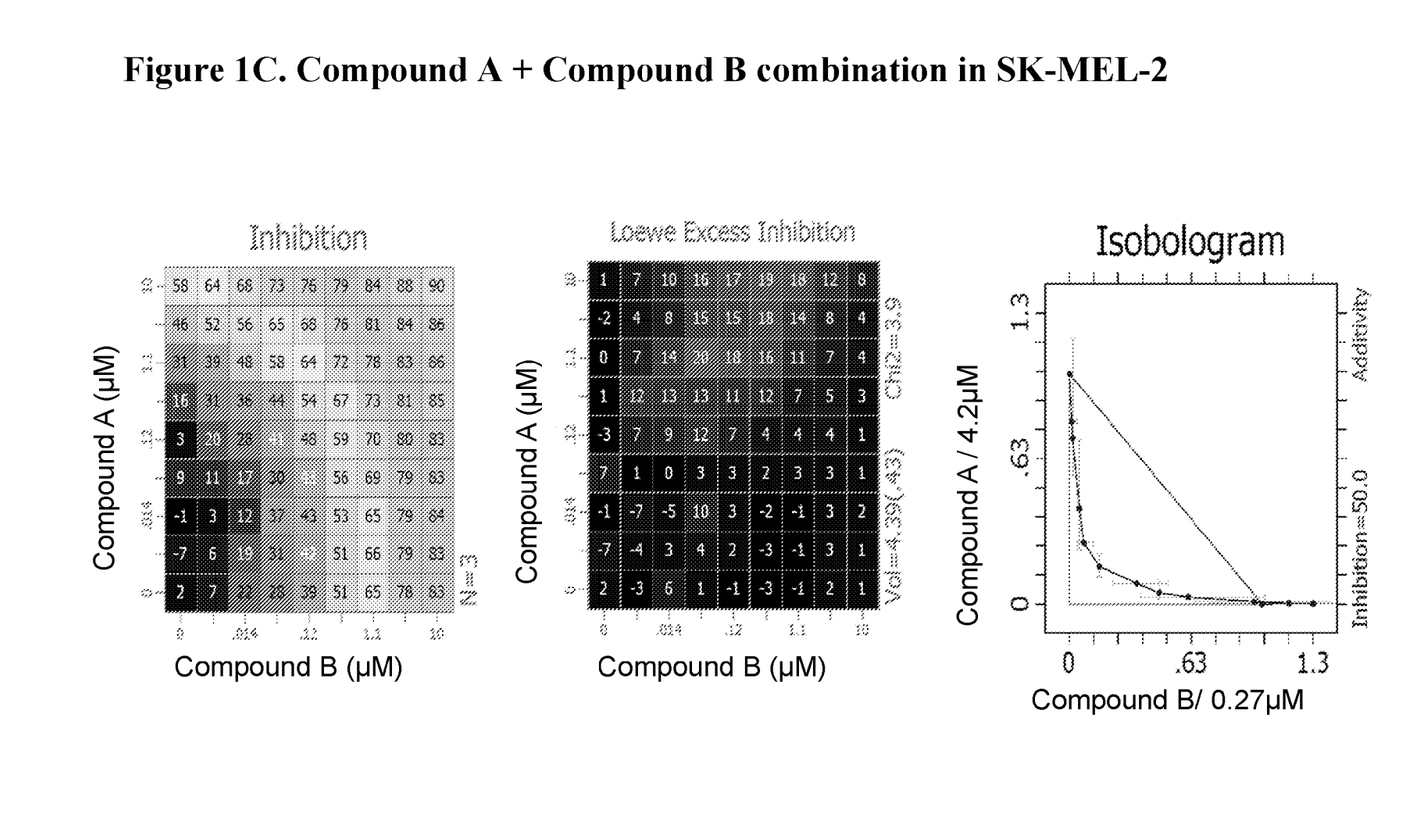
Figure 1D:
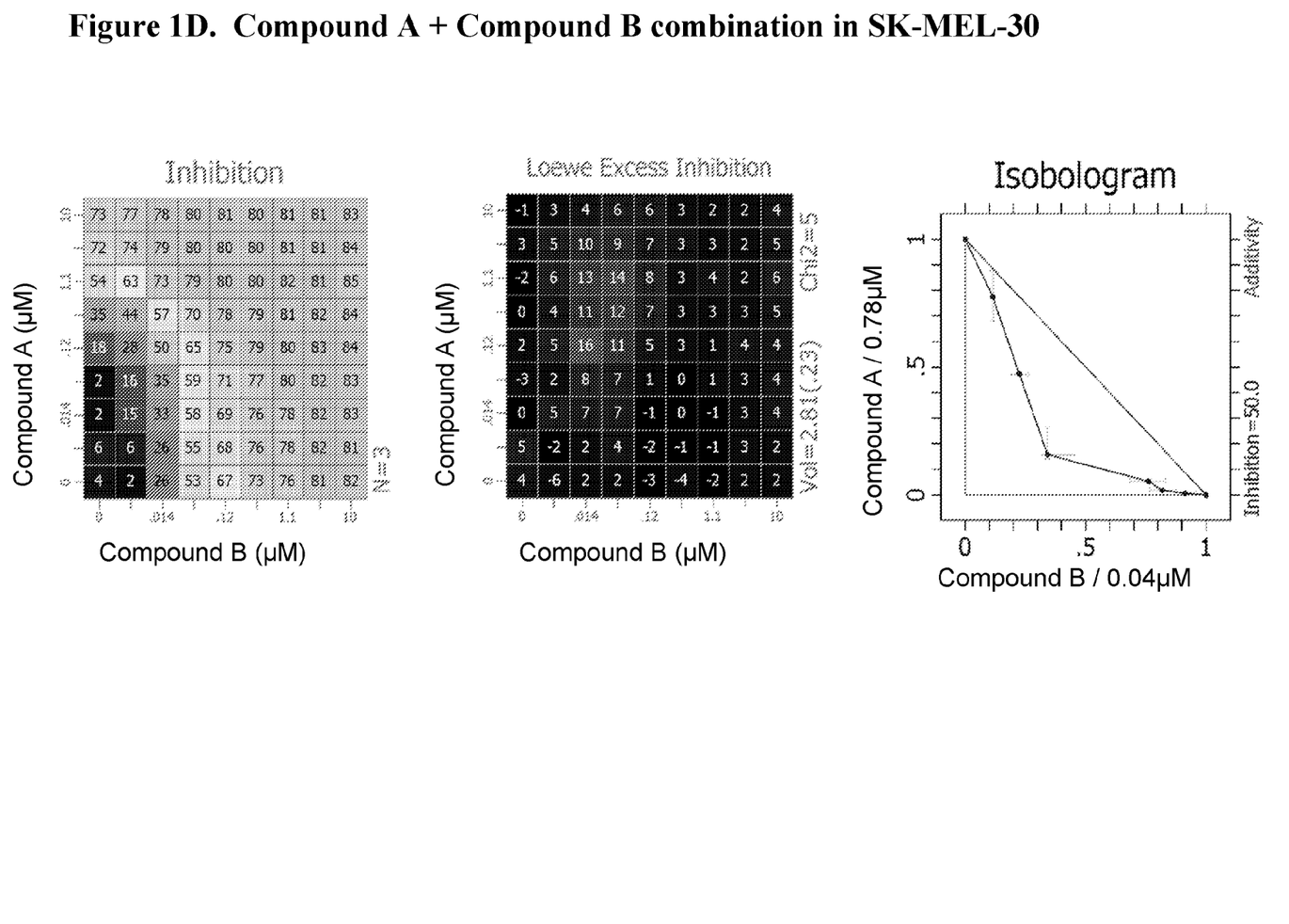
Figure 1E:
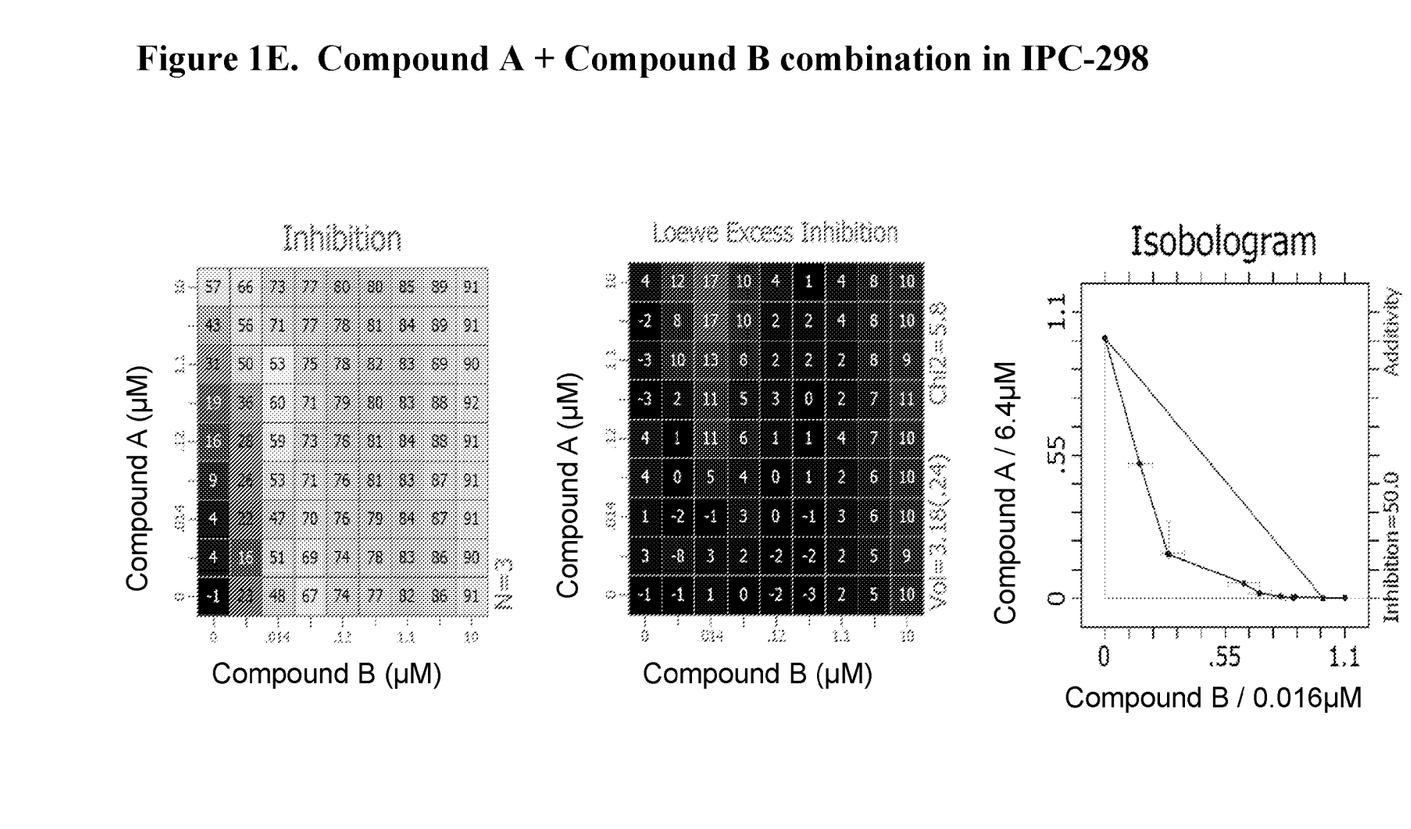
Figure 2:
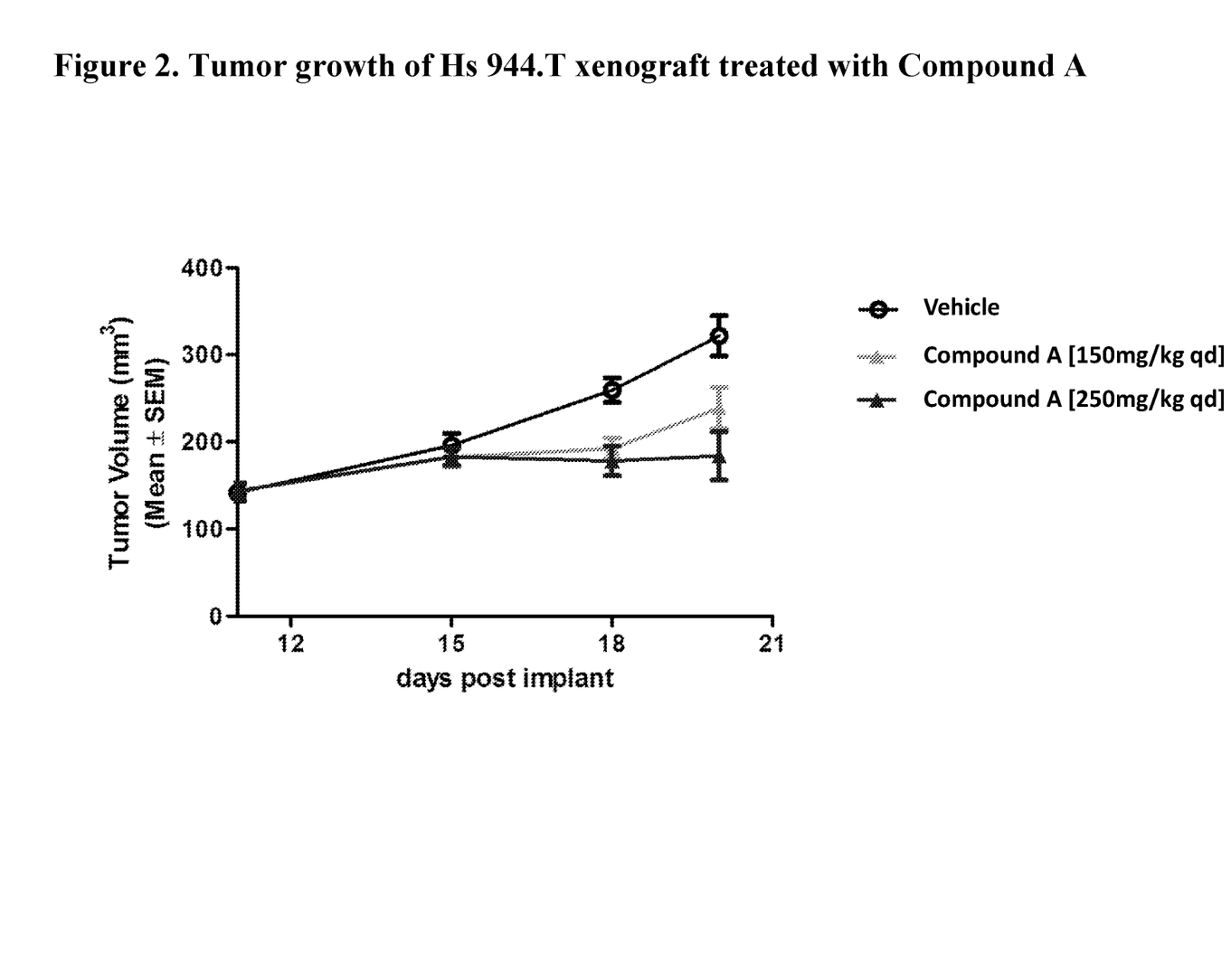
FIG. 2 shows Tumor growth of Hs 944.T xenograft treated with Compound A.

As shown in FIG. 2 and Table 3, animals treated orally with Compound A, at 150 or 250 mg/kg once daily, resulted in T/C=36% or 19%, respectively, in a mouse Hs 944.T xenograft model (p<0.05 compared to vehicle controls).

TABLE 3

Summary results of Compound A efficacy in Hs 944.T xenografts in nude mice

| Treatment | T/C % | Change in tumor volume (mm$^3$, mean ± SEM) | Change in body weight (%, mean ± SEM) | Survival |
|---|---|---|---|---|
| Vehicle | 100 | 242 ± 13 | −10.3 ± 1.2 | 8/8 |
| Compound A, 150 mg/kg qd | 36 | 86 ± 17 | −12.7 ± 2.1 | 5/8 |
| Compound A, 250 mg/kg qd | 19 | 45 ± 25 | −19.7 ± 0.6 | 5/8 |

Three animals each from the 150 mg/kg and 250 mg/kg Compound A treatment groups were classified as TR deaths due to body weight loss criteria, and excluded from data analysis.

Figure 3:
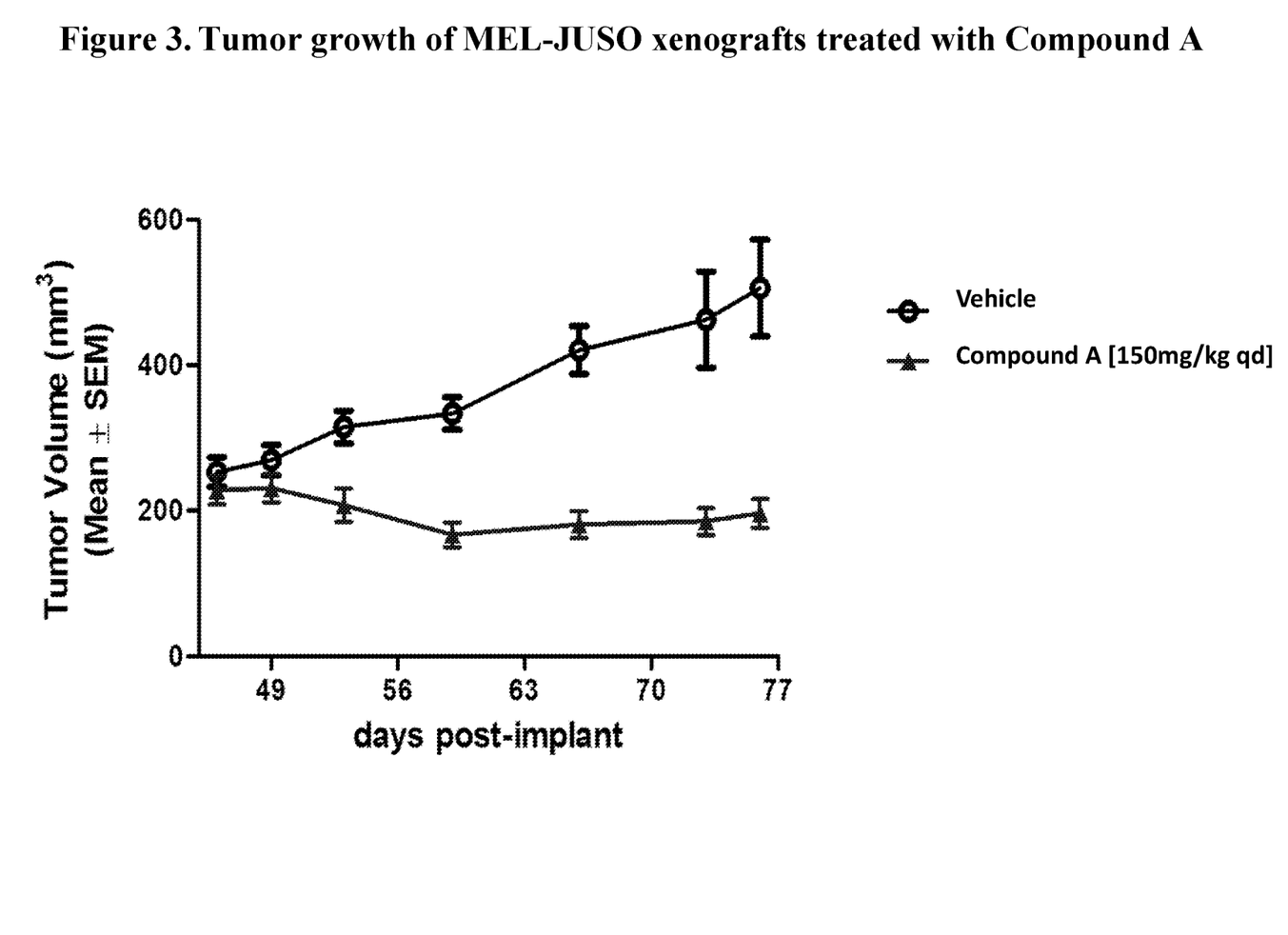
FIG. 3 shows Tumor growth of MEL-JUSO xenografts treated with Compound A.

As shown in FIG. 3 and Table 4, animals treated orally with Compound A, at 150 mg/kg once daily, resulted in 14% tumor regressions in a mouse MEL-JUSO xenograft model (p<0.05 compared to vehicle controls).

TABLE 4

Summary results of Compound A efficacy in MEL-JUSO xenografts in SCID-beige mice

| Treatment | T/C % | Change in tumor volume (mm$^3$, mean ± SEM) | Change in body weight (%, mean ± SEM) | Survival |
|---|---|---|---|---|
| Vehicle | 100 | 254 ± 59 | −16.2 ± 2.2 | 5/6 |
| Compound A, 150 mg/kg qd | 14% reg | −32 ± 14 | −7.3 ± 1.2 | 6/6 |

One vehicle-treated animal was classified as TR death due to body weight loss criteria and excluded from data analyses.

Example 4

Figure 4:
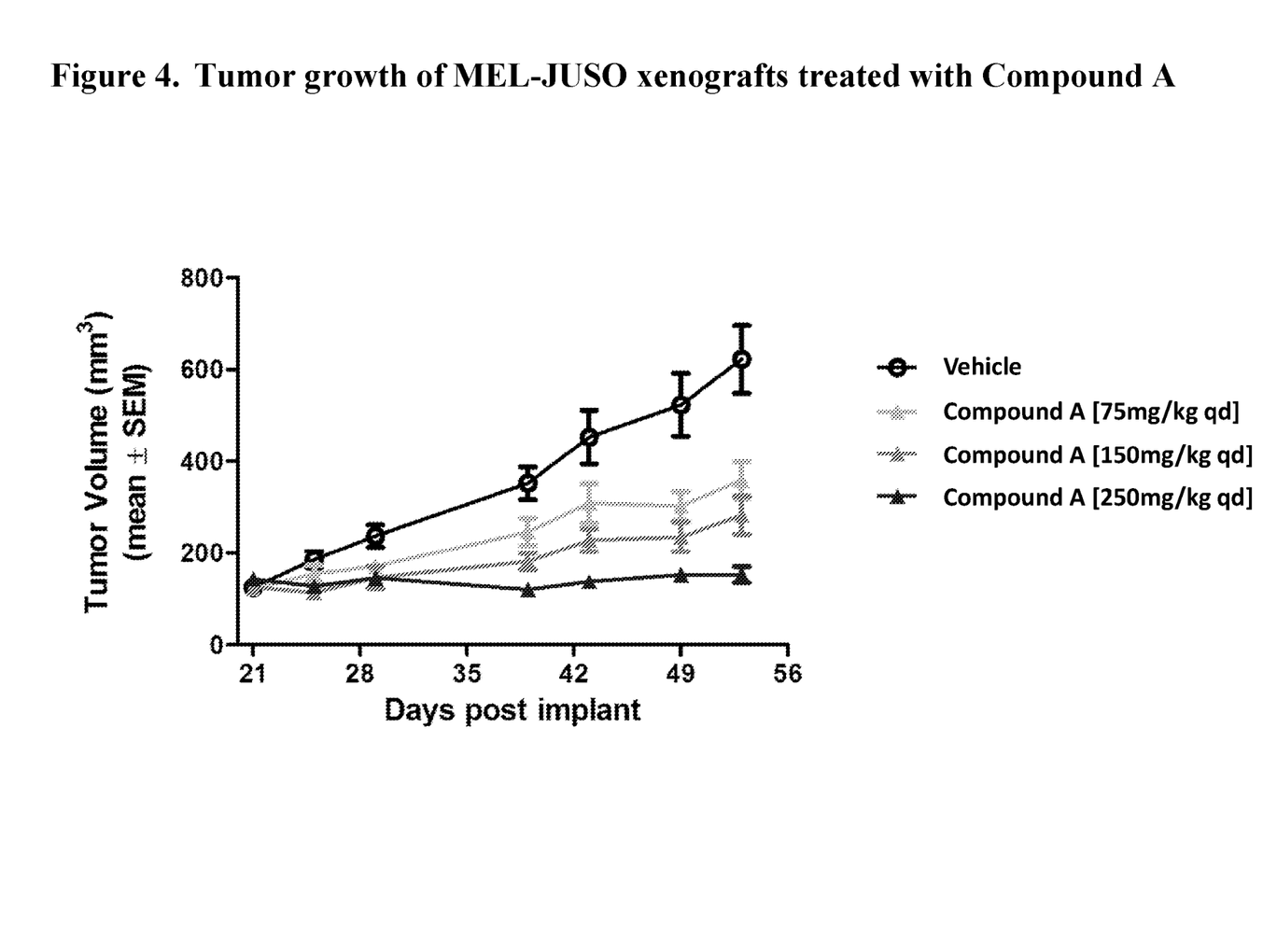
FIG. 4 shows Tumor growth of MEL-JUSO xenografts treated with Compound A
Figure 5:
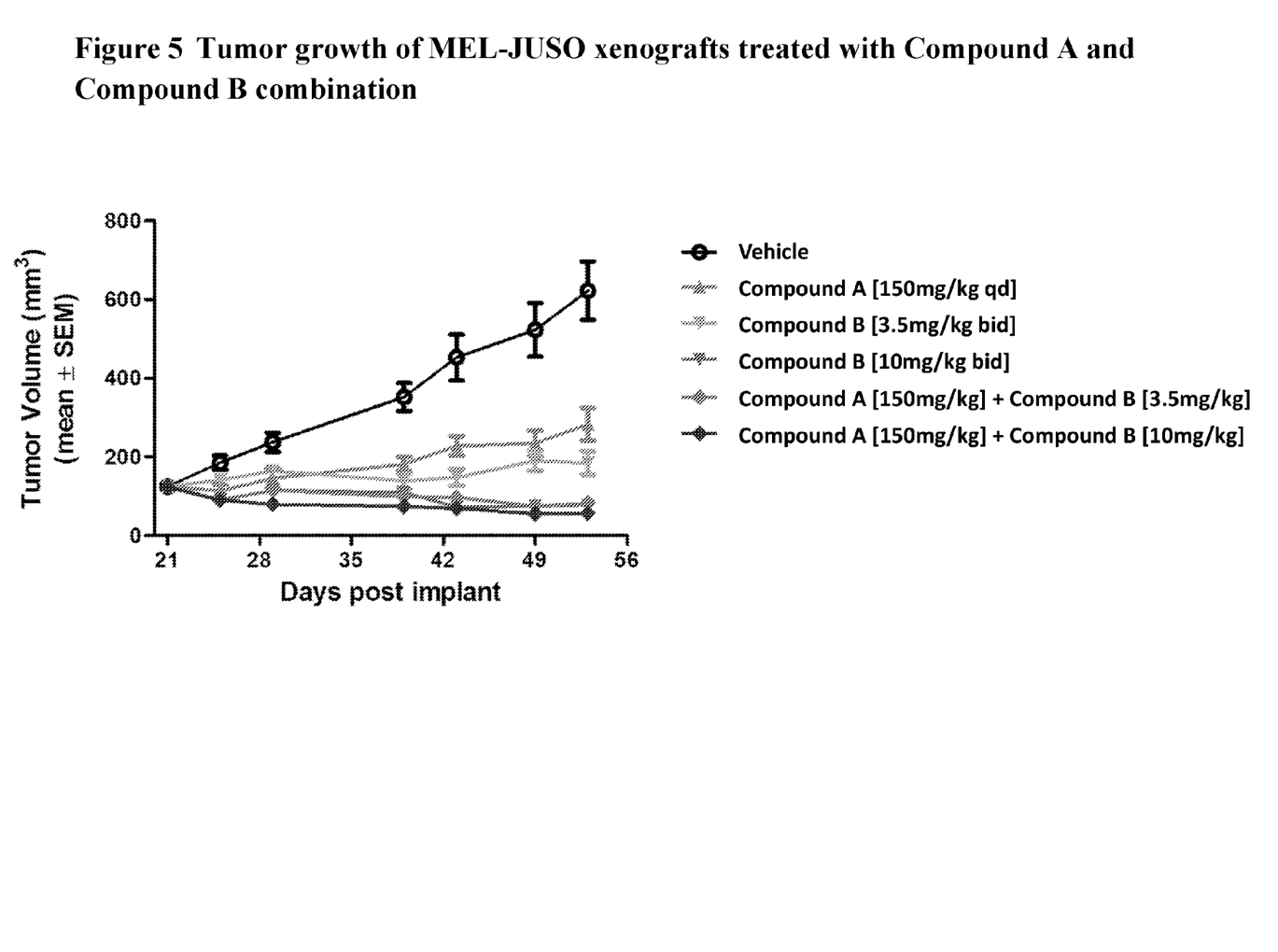
FIG. 5 shows Tumor growth of MEL-JUSO xenografts treated with Compound A and Compound B combination.

Anti-Tumor Efficacy of Compound A and Compound B Combination in MEL-JUSO Xenografts All treatments were well-tolerated by the animals with no significant body weight loss observed over the duration of the study (Table 5). As shown in FIG. 4, animals treated orally, once daily with Compound A, at 75, 150, or 250 mg/kg once daily, resulted in dose-related anti-tumor activity corresponding to T/C=47, 32, or 2%, respectively (p<0.05 only for 250 mg/kg Compound A treatment group compared to vehicle controls). As shown in FIG. 5 and Table 5, animals treated orally, twice daily with Compound B, at 3.5 or 10 mg/kg twice daily, resulted in T/C=12% or 38% tumor regressions, respectively (p<0.05 only for 10 mg/kg Compound B treatment group compared to vehicle controls). The combination of Compound A at 150 mg/kg and Compound B at 3.5 or 10 mg/kg resulted in 34% and 54% tumor regressions, respectively (p>0.05 for combination groups compared to either Compound B alone group). These data suggest that the combination of Compound A and Compound B treatment may lead to robust tumor growth inhibition in NRAS melanoma.

TABLE 5

Summary results of Compound A and Compound B efficacy in MEL-JUSO xenografts

| Treatment | T/C (%) | Regression (%) | Change in tumor volume (mm$^3$, mean ± SEM) | Change in body weight (%, mean ± SEM) | Survival |
|---|---|---|---|---|---|
| Vehicle | 100 | | 497 ± 67 | −4.4 ± 2.1 | 6/6 |
| Compound A [75 mg/kg qd] | 47 | | 236 ± 32 | −3.9 ± 1.5 | 6/6 |
| Compound A [150 mg/kg qd] | 32 | | 157 ± 33 | −3.9 ± 2.1 | 6/6 |
| Compound A [250 mg/kg qd] | 2 | | 9 ± 11 | −2.7 ± 1.6 | 6/6 |
| Compound B [3.5 mg/kg bid] | 12 | | 59 ± 24 | −0.3 ± 2.1 | 6/6 |
| Compound B [10 mg/kg bid] | | 38 | −47 ± 11 | 5.1 ± 1.1 | 6/6 |
| Compound A [150 mg/kg qd] + Compound B [3.5 mg/kg bid] | | 34 | −42 ± 8 | 6.2 ± 2.0 | 6/6 |
| Compound A [150 mg/kg qd] + Compound B [10 mg/kg bid] | | 54 | −67 ± 9 | 8.5 ± 1.5 | 6/6 |

What is claimed is:

1. A combination comprising
(a) a first agent Compound A of Formula A

Formula A or a pharmaceutically acceptable salt thereof and
(b) a second agent Compound B of Formula B Formula B or a pharmaceutically acceptable salt thereof.

2. The combination of claim 1 further comprising one or more excipients.

3. The combination of claim 1 wherein the first agent is the succinate salt of Compound A.

4. The combination of claim 1 wherein Compound A and Compound B are administered simultaneously.

5. The combination of claim 1 wherein Compound A and Compound B are administered separately.

6. The combination of claim 1 wherein Compound A and Compound B are administered sequentially.

7. A method of treating cancer comprising administer to a subject in need of such treatment
(a) a first agent Compound A of Formula A Formula A or a pharmaceutically acceptable salt thereof and
(b) a second agent Compound B of Formula B Formula B or a pharmaceutically acceptable salt thereof.

8. The method of claim 7, wherein the cancer is a solid tumor cancer.

9. The method of claim 8, wherein the cancer is pancreatic cancer, breast cancer, mantle cell lymphoma, non-small cell lung cancer, melanoma, colon cancer, esophageal cancer, liposarcoma, multiple myeloma, T-cell leukemia, renal cell carcinoma, gastric cancer, renal cell carcinoma, glioblastoma, hepatocellular carcinoma, gastric cancer, lung cancer, colon cancer or rhabdoid tumor.

10. The method of claim 9, wherein the cancer is pancreatic cancer, breast cancer, or mantle cell lymphoma.

11. The method of claim 9, wherein the cancer is a lymphoma.

12. The method of claim 9, wherein the cancer is rhabdoid tumor.

* * * * *